United States Patent [19]

Cohen

[11] Patent Number: 5,154,613

[45] Date of Patent: Oct. 13, 1992

[54] DENTAL CEMENT FOR A TEMPORARY DENTAL PROSTHESIS OR APPLIANCE AND METHOD FOR REMOVING SAME

[75] Inventor: Brett I. Cohen, Nanuet, N.Y.

[73] Assignee: Essential Dental Systems, Inc., South Hackensack, N.J.

[21] Appl. No.: 566,510

[22] Filed: Aug. 13, 1990

Related U.S. Application Data

[63] Continuation-in-part of Ser. No. 411,559, Sep. 22, 1989, abandoned.

[51] Int. Cl.$^5$ .................. A61C 5/00; A61K 6/08
[52] U.S. Cl. .................. 433/228.1; 433/226; 433/229; 433/9; 523/116
[58] Field of Search ............ 433/229, 228.1, 226, 433/9; 523/116

[56] References Cited

U.S. PATENT DOCUMENTS

| | | |
|---|---|---|
| 3,751,391 | 8/1973 | Smith . |
| 3,804,794 | 4/1974 | Schmitt et al. . |
| 3,856,737 | 12/1974 | Foster et al. . |
| 4,046,578 | 4/1977 | Smith . |
| 4,166,744 | 9/1979 | Smith . |
| 4,209,434 | 6/1980 | Wilson . |
| 4,222,920 | 4/1980 | Crisp . |
| 4,288,355 | 9/1981 | Anderson . |
| 4,337,186 | 6/1982 | Crisp . |
| 4,375,968 | 3/1983 | Manhart . |
| 4,497,926 | 2/1985 | Toy . |
| 4,553,941 | 11/1985 | Assen . |
| 4,615,924 | 10/1986 | Hekal et al. . |
| 4,710,217 | 12/1987 | Bailey et al. . |
| 4,738,722 | 4/1988 | Ibsen et al. . |
| 4,758,163 | 7/1988 | Goldman . |
| 4,758,612 | 7/1988 | Wilson et al. . |
| 4,762,638 | 8/1988 | Dollman . |
| 4,813,876 | 3/1989 | Wang . |

FOREIGN PATENT DOCUMENTS

| | | |
|---|---|---|
| 0192748 | 8/1968 | Japan . |
| 49-38033 | 4/1974 | Japan . |

*Primary Examiner*—V. Millin
*Attorney, Agent, or Firm*—Gottlieb, Rackman & Reisman

[57] ABSTRACT

A dental cement for providing a fixing for a temporary dental prosthesis or appliance is provided. The dental cement includes a metal oxide, a metal hydroxide and an aqueous solution of a polycarboxylic acid. The cement may also include a fatty acid, a polyvinylacetate emulsion and a dimer fatty acid. One or more plasticizers may also be included. Residual dental cement may be removed from the temporary dental prosthesis or appliance when desired by using a dissolving bath containing a metal hydroxide and a chelating agent.

75 Claims, No Drawings

DENTAL CEMENT FOR A TEMPORARY DENTAL PROSTHESIS OR APPLIANCE AND METHOD FOR REMOVING SAME

BACKGROUND

This is a continuation-in-part application of pending application Ser. No. 411,559 filed Sep. 22, 1989 now abandoned.

This invention relates to dental and surgical cements, and more particularly to a dental cement for providing a fixing for a temporary dental prosthesis or appliance. This invention also relates to a dissolving bath which is suitable for removing a dental cement from a temporary dental prosthesis or appliance.

Material which is referred to as surgical or dental cements have many applications in the dental field including adhering restorative materials to a tooth, providing a lining in a tooth cavity, and sealing root canals after endodontic treatment.

One of the more commonly used cements is a phosphate cement, which is prepared by mixing together a zinc oxide powder and a phosphoric acid solution immediately prior to application. Phosphate cements are not completely satisfactory because they are highly acidic and therefore may be harmful to pulp tissue. Additionally, phosphate cements are typically porous and therefore offer no resistance to the penetration of microorganisms.

A second type of dental or surgical cement that has been used is a zinc oxide-eugenol preparation. Although this type of zinc oxide cement is not harmful to pulp tissue, it has a compressive strength that is substantially less then a phosphate cement; thus, a zinc oxide-eugenol cement is unsatisfactory for many uses.

In recent years, traditional phosphate and zinc oxide-eugenol cements have been to some extent displaced by new polycarboxylate dental cements, in which one of the cement-forming ingredients is an aqueous solution of a polycarboxylic acid. Polycarboxylate cements have improved acid and stain-resistance over conventional dental cements and have the additional advantage that they do not irritate pulp tissue.

Previously, the National Research Development Corporation developed a dental cement which included mixing a zinc oxide powder with an aqueous solution of a polyacrylic acid. These cements had greater adhesion characteristics and caused less irritation then prior zinc phosphate cements. However, these cements were only suitable as permanent cements; there was no suggestion that the zinc oxide cement could be used as a fixing for a temporary dental prosthesis or appliance. Accordingly, it would be desirable to provide an improved polycarboxylate cement composition which is suitable as a fixing for a temporary dental prosthesis or appliance. It would also be desirable to provide a method for easily removing residual cement from the temporary dental prosthesis or appliance.

SUMMARY OF THE INVENTION

Generally speaking, in accordance with the invention, a dental cement for providing a fixing for a temporary dental prosthesis or appliance is provided. The cement includes a paste component comprising a metal oxide in an amount between about 2 and 50 weight percent and a metal hydroxide in an amount between about 2 and 35 weight percent. The paste component may also include a fatty acid and a polyvinylacetate compound.

The cement also includes a catalyst component comprising an aqueous solution of a polycarboxylic acid in an amount between about 35 and 75 weight percent. The catalyst component may also include a polyvinylacetate compound and a dimer fatty acid.

The weight percents are based on the total weight of the cement.

The temporary cement of the invention has a number of advantages including the substantial lack of adherence to dentin, high flow characteristics, and a quick setting time.

As part of this invention, the cement may be easily removed or dissolved from the temporary dental prosthesis or appliance by an aqueous bath solution which includes a metal hydroxide with a concentration of between about 0.5 and 3.0 Molar and a chelating agent with a concentration between about 0.25 and 2.0 Molar. After application, the temporary dental prosthesis or appliance is free of residual cement.

Accordingly, it is an object of this invention to provide an improved dental cement which is suitable as a fixing for a temporary dental prosthesis or appliance.

Yet another object of the invention is to provide an improved dental cement for a temporary dental prosthesis or appliance which is non-irritating.

Another object of the invention is to provide an improved dental cement which is quick setting.

Yet a further object of the invention is to provide an improved dental cement for a temporary dental prosthesis or appliance which does not substantially adhere to dentin.

It is still another object of the invention to provide a dissolving bath which is suitable for removing residual dental cement from a temporary dental prosthesis or appliance.

Still another object of the invention is to provide a dissolving bath for a cement composition which emits no harmful fumes.

A further object of the invention is to provide a dissolving bath for a cement composition which is not harmful to a dental prosthesis or appliance.

Still other objects and advantages of the invention will in part be obvious and will in part be apparent from the following description.

The invention accordingly comprises the several steps and the relation of one or more said steps with respect to each of the others, and the composition or compositions having the features, properties, and the relation of constituents which are exemplified in the following detailed disclosure, and the scope of the invention will be indicated in the claims.

DETAILED DESCRIPTION OF THE PREFERRED EMBODIMENTS

The dental cement of the invention includes a paste or base component consisting of a metal oxide and a metal hydroxide. The metal oxide is present in the cement in an amount between about 2 and 50 weight percent. Preferably, the metal oxide is chosen from zinc oxide, calcium oxide, magnesium oxide, strontium oxide, cadmium oxide, mercury oxide, copper oxide, silver oxide and barium oxide. The preferred metal oxide is zinc oxide which should be present in an amount between about 5 and 40 weight percent.

The purpose of the metal oxide is to form a strong matrix in the cement when the metal oxide chemically combines with the polycarboxylic acid catalyst, as described below.

The metal hydroxide of the paste component is present in the cement of the invention in an amount between about 2 and 35 weight percent, preferably between about 2 and 25 weight percent. The metal hydroxide is chosen from alkali metal hydroxides and alkaline earth metal hydroxides. These include calcium hydroxide, potassium hydroxide, sodium hydroxide, barium hydroxide and magnesium hydroxide. The preferred metal hydroxide is the alkaline earth metal hydroxide calcium hydroxide, which is present in the cement in an amount between about 2 and 25 weight percent.

The function of the metal hydroxide is two fold. The metal hydroxide combines with the polycarboxylic acid component, described below, to form a weak matrix in the cement, which reduces the overall compressive strength of the cement. As a base, the metal hydroxide also buffers the polycarboxylic acid, reducing the acidity of the cement during the setting thereof.

In addition, the metal hydroxide reacts with the chelating agent of the bath, discussed hereinbelow, which causes substantial disintegration of residual cement on the temporary prosthesis or appliance.

The paste or base component of the inventive dental cement may also include a fatty acid in an amount between about 0.1 and 25 weight percent, preferably those chosen from $C_8$ to $C_{18}$ a saturated acids. These fatty acids are generally known in the art as NEO-FAT fatty acids; NEO-FAT is a registered trademark of Akzo Chemie Americas, Inc. of McCook, Ill. for commercially pure $C_8$ to $C_{18}$ a saturated acids, including several grades of oleic (unsaturated) acids (NEO-FAT 90-04, 94-04 and 94-06), and mixtures of fatty acids.

The fatty acid is selected from the fatty acid of caprylic acid (NEO-FAT 8-S), the fatty acid of capric acid (NEO-FAT 10), the fatty acid of lauric acid (NEO-FAT 12-43), the fatty acid of coconut acid (NEO-FAT 255 or 265), the fatty acid of myristic acid (NEO-FAT 14), the fatty acid of palmitic acid (NEO-FAT 16), the fatty acids of stearic acid (NEO-FAT 18 and 18-55) and the fatty acids of oleic acid (NEO-FAT 90-04 (low polyunsaturation) and 90-06). The preferred fatty acid is the fatty acid of lauric acid (NEO-FAT 12-43) which should be present in the cement in an amount between about 0.3 and 10 weight percent.

The function of the fatty acid is two fold. In the first place, the fatty acid increases he adhesion of the cement of the invention by etching the temporary prosthesis or appliance. Once the temporary prosthesis or appliance is etched on the outermost surface thereof (only about 1 mm), the inventive cement can flow into the prosthesis or appliance for adhesion thereto.

In addition, the fatty acid reduces the adhesion of the cement composition of the invention to dentin. As a result, when a temporary appliance is subsequently removed from dental tissue, as described in more detail hereinbelow, residual cement remaining on the tooth surface may be quickly and easily removed.

The paste or base component of the cement composition of the invention may further include homo or copolymers of polyvinylacetate emulsions such as polyvinylacetate (PVA), polyvinylacetate copolymer with ethylene, polyvinylacetate copolymer with butyl acrylate, polyvinylacetate with chrotonic acid, and polyvinylacetate with dibutyl maleate. The polyvinylacetate emulsion of the paste component is present in the cement in an amount between about 0.3 and 15 weight percent. Preferably, the polyvinylacetate emulsion is polyvinylacetate copolymer with ethylene in an amount between about 0.5 and 10 weight percent.

The purpose of the polyvinylacetate emulsion is to increase adhesion of the cement composition to the temporary prosthesis or appliance.

In addition, the inventive cement composition (in the paste or base component) may also include plasticizers (or agents) in an amount up to about 35 weight percent in order to increase flow properties of the cement and to provide body to the paste or base component. Suitable plasticizers include glycerin, stearic acid, zinc stearate, cottonseed oil, rosin, oleic acid, camphor, peanut oil, methylcellulose, ethylcellulose, talc, poly(ethylene oxide), poly(ethylene oxide) derivatives such as tween 20 and tween 80, kaolin, linseed oil, mineral oil, olive oil, corn oil ethoxylated fatty acids of coconut and oleic acid (Peg-15 Cocoate and Peg-10 Oleate), glycine, sodium dodecyl sulfate, sodium carboxymethylcellulose (cellulose gums), food grade xanthan gums, zinc acetate, carbopol resin, karaya gums, tragacanth gums, sprayed dried arabic gums, ethylenebis (oxyethylenenitrilo) tetraacetic acid (EGTA), triethanolamine and corn starch. If one or more plasticizers is added to the cement composition of the invention, the plasticizers should be present in an amount up to about 35 weight percent.

Flavors may be added to the paste of the cement composition in an amount between about 0.1 and 1.0 weight percent. Suitable flavors include orange, wintergreen, cherry, spearmint, peppermint, bubble gum and grape.

The other essential component of the inventive dental cement composition is the catalyst component comprising an aqueous solution of a polycarboxylic acid in an amount between about 35 and 75 weight percent. The aqueous solution of polycarboxylic acid is referred to as the cement-forming liquid and has an average molecular weight of between 30,000 and 120,000.

Suitable polycarboxylic acids include polyacrylic acid, polypropenoic acid, polycinnamic acid, polycrotonic acid, polyisocrotonic acid and polymethacrylic acid. The preferred polycarboxylic acid that is used in the aqueous solution is polyacrylic acid (PAA). If the aqueous solution of a polycarboxylic acid comprises polyacrylic acid, the amount of the aqueous solution in the inventive cement composition is preferably between about 35 and 60 weight percent. The aqueous solution of polyacrylic acid will also have an average molecular weight of between about 40,000 and 80,000. The aqueous solution of polyacrylic acid will comprise between about 30 and 50 percent polyacrylic acid and between about 50 and 70 percent distilled water.

The function of the aqueous solution of polycarboxylic acid is to form a strong matrix with the metal oxide in the overall cement composition, as discussed above.

The aqueous solution of polycarboxylic acid may be prepared by any one of known polymerization techniques. These include polymerization in the presence of ammonium persulphate and the use of various chain transferring agents.

The catalyst component of the inventive cement composition may also include homo or copolymers of polyvinylacetate emulsions such as polyvinylacetate (PVA), polyvinylacetate copolymer with ethylene, polyvinylacetate copolymer with butyl acrylate, polyvinylacetate with chrotonic acid, and polyvinylacetate copolymer with dibutyl maleate. The polyvinylacetate emulsion of the catalyst is present in the cement in an amount between about 0.3 and 30 weight percent. Preferably, the polyvinylacetate emulsion is polyvinylacetate copolymer with ethylene in an amount between about 1.5 and 15 weight percent.

The function of the polyvinylacetate emulsion is to increase adhesion of the temporary cement composition to the temporary prosthesis or appliance.

The catalyst may further include a dimer fatty acid in an amount based on the weight of the inventive cement composition between about 0.2 and 25 weight percent. Preferably, the dimer fatty acid of choice is chosen from an unsaturated $C_{18}$ a dimer fatty acid of oleic acid, a saturated $C_{18}$ a dimer fatty acid of stearic acid, an unsaturated $C_{16}$ dimer fatty acid of palmitoleic acid, a saturated $C_{16}$ dimer fatty acid of palmitic acid, an unsaturated $C_{14}$ dimer fatty acid of myristoleic, and a saturated $C_{14}$ dimer fatty acid of myristic acid. The preferred dimer fatty acid is an unsaturated $C_{18}$ dimer fatty acid of oleic acid in an amount between about 0.5 and 15 weight percent. The function of the dimer fatty acid is to increase the adhesion of the overall cement to the temporary prosthesis or appliance.

A colorant may be added to the catalyst component in an amount between about 0.002 and 0.2 weight percent. Suitable colorants include FD&C yellow #5 and #6, FD&C red #3 and #40, and FD&C blue #1.

As discussed above, the temporary cement in accordance with the invention is biocompatible with pulp tissue. In addition, the cement of the invention is advantageous since it does not adhere to dentin, it is easily removed when placed in the dissolver bath (described hereinafter), has improved flow properties and is quick setting.

The temporary cement of the invention is typically prepared immediately prior to application. The components thereof (metal oxide and metal hydroxide (as well as any others)—paste component; aqueous solution of polycarboxylic acid (as well as any others)—catalyst component) form a mass which may be easily molded, cast, or blown into any desired The following examples are provided in order to illustrate the inventive temporary dental cement.

EXAMPLE 1

| | |
|---|---|
| Zinc Oxide | 24.14 weight percent (1.4 grams) |
| Calcium Hydroxide | 2.76 weight percent (0.16 gram) |
| Rosin | 3.45 weight percent (0.2 gram) |
| Cottonseed Oil | 12.41 weight percent (0.72 gram) |
| Glycerin | 15.86 weight percent (0.92 gram) |
| Polyacrylic Acid | 41.38 weight percent (2.4 grams) |

1.4 grams of zinc oxide were combined with 0.16 gram of calcium hydroxide and 0.2 gram of rosin. Then, 0.92 gram of glycerin and 0.72 gram of cottonseed oil were added to the mixture. The resulting product constituted a light brownish/off-white paste.

Thereafter, 2.4 grams of an aqueous solution of polyacrylic acid (a mixture of 40 percent polyacrylic acid in 60 percent distilled water) were added to the paste. The resulting composition was mixed for approximately 30 seconds to produce an off-white cement composition. The cement composition had a compressive strength of 1622.22 psi after 24 hours at room temperature and a compressive strength of 1208.07 psi after submerger in water for about 24 hours.

EXAMPLE 2

| | |
|---|---|
| Zinc Oxide | 12.29 weight percent (0.5 gram) |
| Calcium Hydroxide | 6.88 weight percent (0.28 gram) |
| Glycerin | 20.88 weight percent (0.85 gram) |
| Peanut Oil | 8.84 weight percent (0.36 gram) |
| Rosin | 3.93 weight percent (0.16 gram) |
| Cottonseed Oil | 2.95 weight percent (0.12 gram) |
| Polyacrylic Acid | 44.23 weight percent (1.8 grams) |

0.5 gram of zinc oxide was combined with 0.28 gram of calcium hydroxide and 0.16 gram of rosin. Then, the 0.85 gram of glycerin, 0.36 gram of peanut oil and 0.12 gram of cottonseed oil were added to the mixture. The resulting product comprised a light brownish/off-white paste.

Thereafter, 1.8 grams of an aqueous solution of polyacrylic acid (a mixture of 40 percent polyacrylic acid in 60 percent water) were added to the paste. The resulting composition was mixed for approximately 30 seconds to produce an off-white cement composition. The cement composition had a compressive strength of 1209.80 psi after 24 hours at room temperature and compressive strength of 854.10 psi after submerger in water for about 24 hours.

EXAMPLE 3

| | |
|---|---|
| Zinc Oxide | 4.68 weight percent (0.44 gram) |
| Calcium Hydroxide | 7.66 weight percent (0.72 gram) |
| Glycerin | 21.28 weight percent (2.00 grams) |
| Peanut Oil | 13.62 weight percent (1.28 grams) |
| Cottonseed Oil | 4.26 weight percent (0.4 gram) |
| Rosin | 5.11 weight percent (0.48 gram) |
| Polyacrylic Acid | 43.40 weight percent (4.08 grams) |

0.44 gram of zinc oxide was combined with 0.72 gram of calcium hydroxide and 0.48 gram of rosin. Then 2.00 grams of glycerin, 1.28 grams of peanut oil and 0.4 gram of cottonseed oil were added to the mixture. The resulting product constituted a light brownish, off-white paste. Thereafter, 4.08 grams of an aqueous solution of polyacrylic acid (a mixture of 40 percent polyacrylic acid in 60 percent distilled water) were added to the paste. The resulting paste was mixed for approximately 30 seconds to produce an off-white cement composition. The cement composition had a compressive strength of 674.10 psi after 24 hours at room temperature and a compressive strength of 351.30 psi after submerger in water for about 24 hours.

EXAMPLE 4

| Zinc Oxide | 21.29 weight percent (1.075 grams) |
|---|---|
| Calcium Hydroxide | 5.94 weight percent (0.30 gram) |
| Rosin | 2.48 weight percent (0.125 gram) |
| Peanut Oil | 20.79 weight percent (1.05 grams) |
| Polyacrylic Acid | 49.50 weight percent (2.5 grams) |

1.075 grams of zinc oxide were combined with 0.30 gram of calcium hydroxide and 0.125 gram of rosin. Then, 1.05 grams of peanut oil was added to the mixture. The resulting product constituted a light brownish, off-white paste.

Thereafter, 2.5 grams of an aqueous solution of polyacrylic acid (a mixture of 40 percent polyacrylic acid in 60 percent distilled water) were added to the paste. The resulting composition was mixed for approximately 30 seconds to produce an off-white cement composition. The cement composition had a compressive strength of 1836.90 psi after 24 hours at room temperature and a compressive strength of 1537.00 psi after submerger in water for about 24 hours.

EXAMPLE 5

| Zinc Oxide | 18.96 weight percent (1.2 grams) |
|---|---|
| Calcium Hydroxide | 5.69 weight percent (0.36 gram) |
| Rosin | 2.37 weight percent (0.15 gram) |
| Zinc Stearate | 2.84 weight percent (0.18 gram) |
| Peanut Oil | 19.91 weight percent (1.26 grams) |
| Polyacrylic Acid | 50.24 weight percent (3.18 grams) |

1.2 grams of zinc oxide were combined 0.36 gram of calcium hydroxide and 0.15 gram of rosin. Then, 1.26 grams of peanut oil and 0.18 gram of zinc stearate were added to the mixture. The resulting product constituted a light brownish, off-white paste.

Thereafter, 3.18 grams of an aqueous solution of polyacrylic acid (a mixture of 40 percent polyacrylic acid in 60 percent distilled water) were added to the paste. The resulting paste was mixed for approximately 30 seconds to produce an off-white cement composition. The cement composition had a compressive strength of 1336.60 psi after 24 hours at room temperature and a compressive strength of 892.90 psi after submerger in water for about 24 hours.

EXAMPLE 6

| Zinc Oxide | 9.24 weight percent (0.66 gram) |
|---|---|
| Calcium Hydroxide | 7.56 weight percent (0.54 gram) |
| Rosin | 2.52 weight percent (0.18 gram) |
| Peanut Oil | 23.53 weight percent (1.68 grams) |
| Zinc Stearate | 6.72 weight percent (0.48 gram) |
| Polyacrylic Acid | 50.42 weight percent (3.6 grams) |

0.66 gram of zinc oxide was combined with 0.54 gram of calcium hydroxide and 0.18 gram of rosin. Then, 0.48 gram of zinc stearate and 1.68 grams of peanut oil were added to the mixture. The resulting product constituted a light brownish, off-white paste.

Thereafter, 3.6 grams of an aqueous solution of polyacrylic acid (a mixture of 40 percent polyacrylic acid in 60 percent distilled water) were added to the paste. The resulting composition was mixed for approximately 30 seconds to produce an off-white cement composition. The cement composition had a compressive strength of 499.00 psi after 24 hours at room temperature and a compressive strength of 418.30 psi after submerger in water for about 24 hours.

EXAMPLE 7

| Magnesium Oxide | 16.60 weight percent (0.83 gram) |
|---|---|
| Magnesium Hydroxide | 8.40 weight percent (0.42 gram) |
| Rosin | 2.60 weight percent (0.13 gram) |
| Peanut Oil | 14.40 weight percent (0.72 gram) |
| Zinc Stearate | 8.00 weight percent (0.40 gram) |
| Polymethacrylic Acid | 50.00 weight percent (2.5 grams) |

0.83 gram of magnesium oxide was combined with 0.42 gram of magnesium hydroxide and 0.13 gram of rosin. Then, 0.40 gram of zinc stearate and 0.72 gram of peanut oil were added to the mixture. The resulting product constituted a light brownish paste.

Thereafter, 2.5 grams of an aqueous solution of polymethacrylic acid (a mixture of 35 percent polymethacrylic acid in 65 percent distilled water) were added to the paste. The resulting composition was mixed for approximately 30 seconds to produce an off white cement composition.

EXAMPLE 8

| Calcium Oxide | 13.27 weight percent (0.71 gram) |
|---|---|
| Magnesium Hydroxide | 7.20 weight percent (0.385 gram) |
| Rosin | 2.52 weight percent (0.135 gram) |
| Peanut Oil | 8.79 weight percent (0.47 gram) |
| Glycerin | 21.50 weight percent (1.15 grams) |
| Polyacrylic Acid | 46.73 weight percent (2.50 grams) |

0.71 gram of calcium oxide was combined with 0.385 gram of magnesium hydroxide and 0.135 gram of rosin. Then, 1.15 grams of glycerin and 0.42 gram of peanut oil were added to the mixture. The resulting product constituted a light brownish paste.

Thereafter, 2.50 grams of an aqueous solution of polyacrylic acid (a mixture of 45 percent polyacrylic acid in 55 percent distilled water) were added to the paste. The paste was mixed for approximately 30 seconds to produce an off-white cement composition.

EXAMPLE 9

| | |
|---|---|
| Zinc Oxide | 5.86 weight percent (0.32 gram) |
| Magnesium Hydroxide | 4.76 weight percent (0.26 gram) |
| Rosin | 4.03 weight percent (0.22 gram) |
| Cottonseed oil | 4.21 weight percent (0.23 gram) |
| Olive Oil | 15.20 weight percent (0.83 gram) |
| Peanut Oil | 13.92 weight percent (0.76 gram) |
| Polycrotonic Acid | 52.01 weight percent (2.84 grams) |

0.32 gram of zinc oxide was combined with 0.26 gram of magnesium hydroxide and 0.22 gram of rosin. Then, 0.83 gram of olive oil, 0.76 gram of peanut oil and 0.23 gram of cottonseed oil were added to the mixture. The resulting product constituted a light brownish paste.

Thereafter, 2.84 grams of an aqueous solution of polycrotonic acid (a mixture of 80 percent polycrotonic acid in 20 percent distilled water) were added to the paste. The resulting composition was mixed for approximately 30 seconds to produce an off-white cement composition.

EXAMPLE 10

| | |
|---|---|
| Zinc Oxide | 19.41 weight percent (16.59 grams) |
| Calcium Hydroxide | 5.18 weight percent (4.43 grams) |
| Rosin | 2.16 weight percent (1.85 grams) |
| Zinc Acetate | 0.19 weight percent (0.16 gram) |
| Poly(ethylene oxide) | 0.21 weight percent (0.18 gram) |
| Neo-Fat 12-43 (fatty acid of lauric acid) | 0.89 weight percent (0.76 gram) |
| Ethylenebis(oxyethylenenitrilo) tetraacetic acid (EGTA) | 0.16 weight percent (0.14 gram) |
| Peanut Oil | 20.24 weight percent (17.30 grams) |
| Polyvinylacetate copolymer with ethylene | 1.15 weight percent (0.98 gram) |
| Triethanolamine | 0.27 weight percent (0.23 gram) |
| Wintergreen Flavor | 0.14 weight percent (0.12 gram) |
| Polyacrylic Acid | 46.77 weight percent (39.98 grams) |
| Polyvinylacetate Copolymer With Ethylene | 3.23 weight percent (2.76 grams) |
| FD & C Yellow #5 | 0.005 weight percent (0.004 gram) |

16.59 grams of zinc oxide were combined with 4.43 grams of calcium hydroxide, 1.85 grams of rosin, 0.18 gram of poly(ethylene oxide), 0.76 gram neo-fat 12-43 (fatty acid of lauric acid), 0.16 gram of zinc acetate, 0.14 gram of ethylenebis(oxyethylenenitrilo) tetraacetic acid (EGTA) and 0.12 gram of wintergreen flavor. Then, 17.30 grams of peanut oil, 0.98 gram of polyvinylacetate copolymer with ethylene, and 0.23 gram of triethanolamine were added to the mixture. The resulting product constituted a light brownish/off-white paste.

Thereafter, 39.98 grams of an aqueous solution of polyacrylic acid (a mixture of 37 percent polyacrylic acid in 63 percent distilled water with an average molecular weight of 80,000), 2.76 grams of polyvinylacetate copolymer with ethylene and 0.004 gram of FD&C yellow #5 were mixed together for a half an hour. After through mixing, the resulting mixture (light yellow-orange) was added to the paste. The resulting paste was mixed for approximately 30 seconds to produce an off-white cement composition.

EXAMPLE 11

| | |
|---|---|
| Zinc Oxide | 11.26 weight percent (9.11 grams) |
| Calcium Hydroxide | 5.46 weight percent (4.42 grams) |
| Rosin | 1.61 weight percent (1.30 grams) |
| Zinc Acetate | 1.68 weight percent (1.36 gram) |
| Zinc Stearate | 4.45 weight percent (3.60 grams) |
| Poly(ethylene oxide) | 0.36 weight percent (0.29 gram) |
| Neo-Fat 12-43 (fatty acid of lauric acid) | 0.94 weight percent (0.70 gram) |
| Ethylenebis(oxyethylenenitrilo)tetraacetic acid (EGTA) | 0.17 weight percent (0.14 gram) |
| Peanut Oil | 22.53 weight percent (18.21 grams) |
| Polyvinylacetate Copolymer With Ethylene | 1.16 weight percent (0.94 gram) |
| Triethanolamine | 0.23 weight percent (0.18 gram) |
| Wintergreen Flavor | 0.14 weight percent (0.11 gram) |
| Polyacrylic Acid | 46.77 weight percent (37.81 grams) |
| Polyvinylacetate Copolymer With Ethylene | 3.23 weight percent (2.61 grams) |
| FD & C Yellow #6 | 0.005 weight percent (0.004 gram) |

9.11 grams of zinc oxide were combined with 4.42 grams of calcium hydroxide, 1.3 grams of rosin, 0.29 gram of poly(ethylene oxide), 0.76 gram of neofat 12-43 (fatty acid of lauric acid), 1.36 grams of zinc acetate, 3.60 grams of zinc stearate, 0.14 gram of ethylenebis(oxyethylenonitrilo) tetraacetic acid (EGTA) and 0.11 gram of wintergreen flavor. Then, 18.21 grams of peanut oil, 0.94 gram of polyvinylacetate copolymer with ethylene, and 0.18 gram of triethanolamine were added to the mixture. The resulting product constituted a light brownish/off-white paste.

Thereafter, 37.81 grams of an aqueous solution of polyacrylic acid (a mixture of 37 percent polyacrylic acid in 63 percent distilled water with average molecular weight of 80,000), 2.61 grams of polyvinylacetate copolymer with ethylene and 0.004 gram of FD&C yellow #6 were mixed together for a half an hour. After through mixing, the resulting mixture (light yellow) was added to the paste. The resulting paste was mixed for approximately 30 seconds to produce an off-white cement composition.

EXAMPLE 12

| | |
|---|---|
| Zinc Oxide | 4.79 weight percent (2.94 grams) |
| Calcium Hydroxide | 6.29 weight percent (3.86 grams) |
| Rosin | 1.68 weight percent (1.03 grams) |
| Zinc Acetate | 2.62 weight percent (1.61 grams) |
| Zinc Stearate | 6.91 weight percent (4.24 grams) |

-continued

| | |
|---|---|
| Poly(ethylene oxide) | 0.37 weight percent (0.23 gram) |
| Neo-Fat 12-43 (fatty acid of lauric acid) | 1.29 weight percent (0.79 gram) |
| Ethylenebis(oxyethylenenitrilo) tetraacetic acid (EGTA) | 0.309 weight percent (0.19 gram) |
| Peanut Oil | 23.47 weight percent (14.41 grams) |
| Polyvinylacetate Copolymer With Ethylene | 1.16 weight percent (0.71 gram) |
| Triethanolamine | 0.407 weight percent (0.25 gram) |
| Wintergreen Flavor | 0.21 weight percent (0.13 gram) |
| Polyacrylic Acid | 46.77 weight percent (28.72 grams) |
| Polyvinylacetate Copolymer With Ethylene | 3.22 weight percent (1.98 grams) |
| Dimer fatty acid of oleic acid | 0.5 weight percent (0.31 gram) |
| FD & C Yellow #5 | 0.007 weight percent (0.004 grams) |

2.94 grams of zinc oxide were combined with 3.86 grams of calcium hydroxide, 1.03 grams of rosin, 0.23 gram of poly(ethylene oxide), 0.79 gram neo-fat 12-43 (fatty acid of lauric acid), 1.61 grams of zinc acetate, 4.24 grams of zinc stearate, 0.19 gram of ethylenebis(oxyethylenenitrilo) tetraacetic acid (EGTA), and 0.13 gram of wintergreen flavor. Then, 14.41 grams of peanut oil, 1.02 grams of polyvinylacetate copolymer with ethylene, and 0.25 gram of triethanolamine were added to the mixture. The resulting product constituted a light brownish/off-white paste.

Thereafter, 28.72 grams of an aqueous solution of polyacrylic acid (a mixture of 37 percent polyacrylic acid in 63 percent distilled water with average molecular weight of 80,000) 1.98 grams of polyvinylacetate copolymer with ethylene and 0.004 gram of FD&C yellow #5 were mixed together for a half an hour. After through mixing, the resulting mixture (light yellow-orange) was added to the paste. The resulting paste was mixed for approximately 30 second to produce an off-white cement composition.

After preparing the desired temporary dental cement composition of the invention, the cement is applied to a dental prosthesis or appliance (such as a crown or bridge). Typically, once the cement is prepared, a small amount is added or applied to the inner surface of the prosthesis or appliance—this is the surface which must attach to the dental tissue. After the cement is applied, the patient is instructed to "bite down" on the prosthesis or appliance, so that the exposed dental tissue contacts the inner surface area of the prosthesis or appliance (where the cement has been applied). This causes the cement to spread along the region of contact between the dental tissue and the prosthesis or appliance. Any excess cement which has leaked past the contact area may be easily scraped away.

The cement of the inventive composition will quickly set with the addition of a small amount of heat. Thus, when the dental appliance or prosthesis is placed in the patient's mouth and applied to the desired dental tissue, the cement that is utilized will set rapidly, within about a minute or so.

When it is desired to remove the temporary prosthesis or appliance from the mouth of the patient, the dentist will utilize a dental instrument for detaching the prosthesis or appliance from the dental tissue. Suitable instruments include an explorer, a probe or a crown remover. If these instruments are operated correctly, the dentist will be able to break the seal between the prosthesis or appliance and the dental tissue.

Reasons why the temporary prosthesis or appliance would be removed include attaching a more permanent prosthesis or appliance to the dental tissue, adjusting the position of the temporary prosthesis or appliance, conducting an impression for later placement of a permanent prosthesis or appliance and removing foreign debris caught between the temporary prosthesis or appliance and the dental tissue.

Many times, a dentist may want to re-use the temporary prosthesis or appliance. The permanent prosthesis or appliance may not be ready and the cost and effort to prepare a new temporary may be substantial. However, before re-using the temporary prosthesis or appliance, it is necessary to remove residual cement remaining thereon, particularly along undercuts in the prosthesis or appliance. This may be achieved using the dissolving bath of the invention, which is described below.

The dissolving bath which is used for removing residual cement of the invention from a temporary dental prosthesis or appliance constitutes an aqueous solution containing a metal hydroxide with a concentration between about 0.5 and 3.0 Molar and a chelating agent with a concentration between about 0.25 and 2.0 Molar.

The metal hydroxide is preferably chosen from an alkali metal hydroxide such as sodium hydroxide and potassium hydroxide. The preferred alkali metal hydroxide is sodium hydroxide. The sodium hydroxide has a concentration in the bath that is preferably between about 1.0 to 2 0 Molar.

The chelating agent is chosen from ethylenediaminetetraacetic acid, disodium salt dihydrate ($Na_2EDTA$); ethylenediaminetetraacetic acid, tetrasodium salt ($Na_4EDTA$); ethylenediaminetetraacetic acid (EDTA); ethylenediaminetetraacetic acid, dipotassium salt dihydrate; sodium tartrate; tartaric acid, dipotassium salt hemihydrate; sodium tartrate; tartaric acid, monosodium salt; dihydroxytartaric acid, disodium salt hydrate; tartronic acid (hydroxy malonic acid); sodium salicylate; salicylic acid; tartaric acid; dihydroxy tartaric acid; trans-1, 2-diaminocyclohexane-N,N, N',N'-tetraacetic acid (CDTA); N,N-bis [2-Hydroxyethyl]-glycine (bicine); 3-hydroxy-4-[[1-hydroxy-2-napthalenyl]azo]-7-nitro-1-naphthalenesulfonic acid monosodium salt; (Erio-chrome Black T); diethylenetriaminepentaacetic acid, 8-hydroxyquinoline; 8-hydroxyquinoline-5-sulfonic acid; maleic acid; citric acid; and N-[2-hydroxyethyl] imino-diacetic acid (HIMDA).

The preferred chelating agent is $Na_2EDTA$ which will have a concentration in the bath that is from 0.50 to 1.25 Molar.

The purpose of the metal hydroxide in the bath is to chemically breakdown the metal oxide-polycarboxylic acid matrix (strong) by hydrolyzing the metal-acid bond found in this matrix. The function of the chelating agent in the bath is to chemically bond with the metal hydroxide in the cement and to breakdown the matrix (weak) formed between the cement metal hydroxide and polycarboxylic acid.

Optionally, the bath of the invention may include a chemical indicator which changes color when the bath no longer effectively dissolves residual cement (after numerous uses of the bath for dissolving the cement).

The following examples are given to illustrate the bath of the invention.

EXAMPLE 13

Sodium Hydroxide (3M)
Na$_2$EDTA (1M)

12.00 grams of sodium hydroxide were added to 100 ml of distilled water. Then, 37.28 grams of ethylenediamenetetraacetic acid, disodium salt dihydrate (Na$_2$EDTA) were added to the solution. The resulting solution or bath was stirred for about one hour until all the Na$_2$EDTA dissolved.

EXAMPLE 14

Sodium Hydroxide (1M)
Na$_2$EDTA (0.523M)
7 ml of stock solution of Mordant Orange 6

4.00 grams of sodium hydroxide were added to 100 ml of distilled water. 19.46 grams of Na$_2$EDTA were then added to the solution. The resulting solution or bath was stirred for about one hour until all the Na$_2$EDTA dissolved.

Thereafter, 7 ml of stock solution of Mordant Orange 6 (0.05 gram of Mordant Orange 6 and 150 ml of distilled water) were added to the bath, which was stirred for another 30 minutes. The pH of the bath was approximately 9.63.

A cement manufactured in accordance with the invention was added to the bath, causing the pH of the bath to rise. When the pH reached a level between 10.8 and 11.5, the color of the bath changed from a golden-yellow to red (which indicated that the bath had been deactivated and needed to be replaced).

EXAMPLE 15

Sodium Hydroxide (1.05M)
Na$_2$EDTA (0.530M)
7 ml of stock solution of Mordant Orange 6

4.19 grams of sodium hydroxide were added to 100 ml of distilled water. Then, 19.72 grams of Na$_2$EDTA were added to the solution. The resulting solution or bath was stirred for about one hour.

7 ml of stock solution of Mordant Orange 6 (0.05 gram of Mordant Orange 6 and 150 ml of distilled water) were then added to the bath, which was stirred for an additional 30 minutes. The pH of the bath was approximately 9.80.

It has been found that the amount of cement made in accordance with the invention which is needed to deactivate (render it unusable) the bath is proportional to the number of days that the bath has been used. For the bath of Example 14, an average number of 11 bridge appliances were added each day to the bath over a four day period. Each bridge appliance had approximately 0.3 gram of cement made in accordance with the invention. Thus, the total amount of residual cement to which the bath was exposed over the four days was about 13.2 grams. It was found that the bath became de-activated at the end of that four day period—the color of the bath solution changed from yellow-golden to red. In contrast, with respect to the bath in Example 15, that bath de-activated in about two days (the bath was exposed to 6.6 grams of the cement made in accordance with the invention).

The dissolving bath of the invention is advantageous since it dissolves residual cement remaining on the temporary prosthesis or appliance without harming the temporary prosthesis or appliance. Most temporary prostheses or appliances are made of an acrylic material, which is unaffected by the bath composition.

In addition, the bath is advantageous since it emits no harmful odors or fumes which might otherwise limit its application.

In use, the temporary prosthesis or appliance is placed in the bath composition. The entire combination is placed into a conventional ultrasound machine for a few minutes. Use of an ultrasound machine is preferable since it promotes equal mixing of all reagents. When removed from the ultrasound machine, the temporary prosthesis or appliance is free of all residual cement.

The following examples illustrate the effectiveness of the bath in dissolving residual cement remaining on an acrylic prosthesis or appliance:

EXAMPLE 16

| Acrylic Sample | Applied Cement & Acrylic Sample | Acrylic Placed in Bath |
|---|---|---|
| 1.61 grams | 1.88 grams | 1.63 grams |
| 2.25 grams | 2.60 grams | 2.26 grams |
| 1.91 grams | 2.20 grams | 1.94 grams |
| 2.55 grams | 2.85 grams | 2.57 grams |
| 2.55 grams | 2.92 grams | 2.56 grams |

Each acrylic sample was applied with the cement described in Example 4 (described hereinabove). After application, the acrylic sample was placed in the dissolving bath described in Example 15. The bath was then placed in an ultrasound machine and mixed for about 20 minutes. Upon removal from the ultrasound machine, each acrylic sample was rinsed with tap water and then air dried for about 30 minutes and weighed to determine how much cement remained thereon. As shown, virtually all the cement that was applied to each acrylic sample was removed by the bath.

As a control, a series of acrylic samples were placed in the dissolving bath described in Example 15 without application of any cement composition:

| Control Acrylic Sample | Control Acrylic After Placed In Bath |
|---|---|
| 2.22 grams | 2.22 grams |
| 1.74 grams | 1.75 grams |
| 1.87 grams | 1.88 grams |

None of the control acrylic samples exhibited any weight loss, demonstrating that the bath has no effect on an acrylic prosthesis or appliance.

EXAMPLE 17

| Acrylic Sample Bath | Applied Cement & Acrylic Sample | Acrylic After Placed in |
|---|---|---|
| 1.63 grams | 1.91 grams | 1.64 grams |
| 2.46 grams | 2.90 grams | 2.49 grams |
| 1.48 grams | 1.76 grams | 1.49 grams |
| 2.07 grams | 2.58 grams | 2.07 grams |
| 1.37 grams | 1.60 grams | 1.42 grams |

Each acrylic sample was applied with the cement described in Example 5 (described hereinabove). After application, the acrylic sample was placed in the dissolving bath described in Example 15. The bath was then placed in an ultrasound machine and mixed for about 20 minutes. Upon removal from the ultrasound machine, each acrylic sample was rinsed with tap water and then air dried for about 30 minutes and weighed to determine how much cement remained thereon. As shown, virtually all the cement that was applied to each acrylic sample was removed by the bath.

As a control, a series of acrylic samples were placed in the dissolving bath described in Example 15 without application of any cement composition:

| Control Acrylic Sample | Control Acrylic After Placed In Bath |
| --- | --- |
| 2.24 grams | 2.26 grams |
| 1.75 grams | 1.75 grams |
| 2.23 grams | 2.23 grams |

None of the control acrylic samples exhibited any weight loss, demonstrating that the bath has no effect on an acrylic prosthesis or appliance.

EXAMPLE 18

| Acrylic Sample | Applied Cement & Acrylic Sample | Acrylic After Placed In Bath |
| --- | --- | --- |
| 2.55 grams | 2.90 grams | 2.60 grams |
| 2.23 grams | 2.54 grams | 2.25 grams |
| 2.07 grams | 2.38 grams | 2.10 grams |
| 0.97 gram | 1.26 grams | 0.99 gram |
| 1.40 grams | 1.72 grams | 1.42 grams |

Each acrylic sample was applied with the cement described in Example 6 (described hereinabove). After application, the acrylic sample was placed in the dissolving bath described in Example 15. The bath was then placed in an ultrasound machine and mixed for about 20 minutes. Upon removal from the ultrasound machine, each acrylic sample was rinsed with tap water and then air dried for about 30 minutes and weighed to determine how much cement remained thereon. As shown, virtually all the cement that was applied to each acrylic sample was removed by the bath.

As a control, a series of acrylic samples were placed in the dissolving bath described in Example 15 without application of any cement composition:

| Control Acrylic Sample | Control Acrylic After Placed In Bath |
| --- | --- |
| 1.87 grams | 1.87 grams |
| 1.74 grams | 1.75 grams |
| 2.55 grams | 2.55 grams |

None of the control acrylic samples exhibited any weight loss, demonstrating that the bath has no effect on an acrylic prosthesis or appliance.

It will thus be seen that the objects set forth above, among those made apparent from the preceding description, are efficiently attained, and since certain changes may be made in carrying out the above method and in preparing the composition as set forth above without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A dental cement for providing a fixing for a temporary dental prosthesis or appliance comprising:
   a metal oxide in an amount between about 2 and 50 weight percent;
   a metal hydroxide in an amount between about 2 and 35 weight percent; and
   an aqueous solution of a polycarboxylic acid in an amount between about 35 and 75 weight percent.

2. The cement of claim 1, wherein said metal oxide is selected from the group including zinc oxide, calcium oxide, magnesium oxide, strontium oxide, cadmium oxide, mercury oxide, copper oxide, silver oxide and barium oxide 3. The dental cement of claim 2, wherein said metal oxide is zinc oxide in an amount between about 5 and 40 weight percent.

4. The dental cement of claim 1, wherein the metal hydroxide is in an amount between about 2 and 25 weight percent 5. The dental cement of claim 4, wherein said metal hydroxide is selected from the group including alkali metal hydroxides and alkaline earth metal hydroxides.

6. The dental cement of claim 5, wherein said alkali metal hydroxides are selected from the group including potassium hydroxide and sodium hydroxide.

7. The cement of claim 5, wherein said alkaline earth metal hydroxides are selected from the group including calcium hydroxide, barium hydroxide and magnesium hydroxide.

8. The cement of claim 7, wherein said alkaline earth metal hydroxide is calcium hydroxide in an amount between about 2 and 25 weight percent.

9. The cement of claim 1, further including a fatty acid in an amount between about 0.1 and 25 weight percent.

10. The cement of claim 9, wherein the fatty acid is selected from $C_8$ to $C_{18}$ a saturated acids.

11. The cement of claim 10, wherein the fatty acid is selected from the group including the fatty acid of caprylic acid, the fatty acid of cupric acid, the fatty acid of lauric acid, the fatty acid of coconut acid, the fatty acid of myristic acid, the fatty acid of palmitic acid, the fatty acids of stearic acid and the fatty acids of oleic acid.

12. The cement of claim 11, wherein the fatty acid is the fatty acid of lauric acid in an amount between about 0.3 and 10 weight percent.

13. The cement of claim 1, further including a polyvinylacetate emulsion in an amount between about 0.6 and 45 weight percent.

14. The cement of claim 13, wherein the polyvinylacetate emulsion is selected from the group including polyvinylacetate and polyvinylacetate copolymer with ethylene.

15. The cement of claim 14, wherein the polyvinylacetate emulsion is polyvinylacetate copolymer with ethylene in an amount between about 2 and 25 weight percent.

16. The cement of claim 1, further including a plasticizer in an amount up to about 35 weight percent.

17. The cement of claim 16, wherein said plasticizer is selected from the group including glycerin, stearic acid, zinc stearate, cottonseed oil, rosin, oleic acid, camphor, peanut oil, methycellulose, ethylcellulose, talc, poly(ethyleneoxide), poly(ethyleneoxide) derivatives, kaolin, linseed oil, minmineral oil, olive oil, corn oil, ethyoxlated fatty acids of coconut and oleic acid, glycine, sodium dodecyl sulfate, sodium carboxymethylcellulose, food grade xanthan gums, zinc acetate, carbopol resin, karaya gums, tragacanth gums, sprayed dried arabic gums, ethylenebis (oxyethylenenitrilo) tetraacetic acid, triethanolamine and corn starch.

18. The cement of claim 1, further including flavors in an amount between about 0.1 and 1.0 weight percent.

19. The cement of claim 18, wherein the flavors are selected from the group including orange, wintergreen, cherry, spearmint, peppermint, bubble gum and grape.

20. The cement of claim 1, wherein said polycarboxylic acid has an average molecular weight of between about 30,000 and 120,000 and is selected from the group including polyacrylic acid, polypropenoic acid, polycinnamic acid, polycrotonic acid, polyisocrotonic acid and polymethacrylic acid.

21. The cement of claim 20, wherein said polycarboxylic acid is polyacrylic acid.

22. The cement of claim 21, wherein said aqueous solution of polyacrylic acid is present in an amount between about 35 and 60 weight percent.

23. The cement of claim 22, wherein said aqueous solution of polyacrylic acid includes polyacrylic acid having an average molecular weight of between about 40,000 and 80,000.

24. The cement of claim 22, wherein said aqueous solution of polyacrylic acid includes polyacrylic acid in an amount between about 35 and 60 weight percent as compared to the total weight of the aqueous solution.

25. The cement of claim 1, further including a dimer fatty acid in an amount between about 0.2 and 25 weight percent.

26. The cement of claim 25, wherein the dimer fatty acid is selected from the group including an unsaturated $C_{18}$ dimer fatty acid of oleic acid, a saturated $C_{18}$ a dimer fatty acid of stearic acid, an unsaturated $C_{16}$ dimer fatty acid of palmitoleic acid, a saturated $C_{16}$ dimer fatty acid of palmitic acid, an unsaturated $C_{14}$ dimer fatty acid of myristoleic acid, and a saturated $C_{14}$ dimer fatty acid of myristic acid.

27. The cement of claim 26, wherein the dimer fatty acid is an unsaturated $C_{18}$ dimer fatty acid of oleic acid in an amount between about 0.5 and 15 weight percent.

28. The cement of claim 1, further including a colorant in an amount between about 0.002 and 0.2 weight percent.

29. The cement of claim 1, wherein
said metal oxide comprises zinc oxide in an amount between about 5 and 40 weight percent;
said metal hydroxide comprises calcium hydroxide in an amount between about 2 and 25 weight percent; and
said aqueous solution of a polycarboxylic acid comprises an aqueous solution of polyacrylic acid in an amount between about 35 and 60 weight percent.

30. The cement of claim 29, further including:
the fatty acid of lauric acid in an amount between about 0.3 and 10 weight percent;
polyvinylacetate copolymer with ethylene in an amount between about 2.0 and 25 weight percent; and
an unsaturated $C_{18}$ dimer fatty acid of oleic acid in an amount between about 0.5 and 15 weight percent.

31. The cement of claim 1, further including:
a fatty acid in an amount between about 0.1 and 25 weight percent;
a polyvinylacetate emulsion in an amount between about 0.6 and 45 weight percent; and
a dimer fatty acid in an amount between about 0.2 and 25 weight percent.

32. The cement of claim 31, further including a plasticizer in an amount up to about 35 weight percent.

33. A dental cement for providing a fixing for a temporary dental prosthesis or appliance comprising a paste component and a catalyst component, wherein:
said paste component includes a metal oxide in an amount between about 2 and 50 weight percent and a metal hydroxide in an amount between about 2 and 35 weight percent;
said catalyst component includes an aqueous solution of a polycarboxylic acid in an amount between about 35 and 75 weight percent;
said paste being formed by adding said catalyst component to said base component; and
said weight percents being based on the weight of said formed paste.

34. The dental cement of claim 33, wherein said metal oxide is zinc oxide in an amount between about 5 and 40 weight percent.

35. The dental cement of claim 33, wherein the metal hydroxide is calcium hydroxide in an amount between about 2 and 25 weight percent.

36. The dental cement of claim 33, wherein the aqueous solution of polycarboxylic acid comprises an aqueous solution of polyacrylic acid in an amount between about 35 and 60 weight percent.

37. The dental cement of claim 33, wherein the paste component further includes a fatty acid in an amount between about 0.1 and 25 weight percent.

38. The dental cement of claim 37, wherein the fatty acid is the fatty acid of lauric acid in an amount between about 0.3 and 10 weight percent.

39. The dental cement of claim 33, wherein the paste component further includes a polyvinylacetate emulsion in an amount between about 0.3 and 15 weight percent.

40. The dental cement of claim 39, wherein the polyvinylacetate emulsion is polyvinylacetate copolymer with ethylene in an amount between about 0.5 and 10 weight percent.

41. The dental cement of claim 33, wherein said paste component further includes a plasticizer in an amount up to about 35 weight percent.

42. The dental cement of claim 33, wherein said catalyst component includes a polyvinylacetate emulsion in an amount between about 0.3 and 30 weight percent.

43. The dental cement of claim 42, wherein the polyvinylacetate emulsion is selected from the group including polyvinylacetate, polyvinylacetate copolymer with ethylene, polyvinylacetate copolymer with butyl acrylate, polyvinylacetate with chrotonic acid, and polyvinylacetate with dibutyl maleate.

44. The dental cement of claim 33, wherein said catalyst component further includes a dimer fatty acid in an amount between about 0.2 and 25 weight percent.

45. The dental cement of claim 44, wherein the dimer fatty acid is an unsaturated C's dimer fatty acid of oleic acid in an amount between about 0.5 and 15 weight percent.

46. A dissolving bath for removing residual cement from a temporary dental prosthesis or appliance comprising an aqueous solution containing a metal hydroxide with a concentration of between about 0.5 and 3.0 Molar and a chelating agent with a concentration of between about 0.25 and 2.0 Molar.

47. The bath of claim 46, wherein said metal hydroxide is an alkali metal hydroxide selected from the group including sodium hydroxide and potassium hydroxide.

48. The bath of claim 47, wherein said alkali metal hydroxide is sodium hydroxide having a concentration in solution of between about 1 and 2 Molar.

49. The bath of claim 46, wherein said chelating agent is selected from the group including ethylenediamine tetraacetic acid, disodium salt dihydrate; ethylenediamine tetraacetic acid, tetrasodium salt; ethylenediaminetetraacetic acid; ethylene diaminetetraacetic acid, dipotassium salt dihydrate; sodium tartrate; tartaric acid, dipotassium salt hemihydrate; sodium bitartrate; tartaric acid, monosodium salt; dihydroxy tartaric acid; disodium salt hydrate; tartartronic acid; sodium salicylate; salicylic acid; tartaric acid; dihydroxy tartaric acid; trans-1, 2-diaminecyclohexane-N-N-N'-N'-tetraacetic acid; N-N-bis[2-hydroxethyl]-glycine; 3-hydroxy-4-[[1-hydroxy-2-napthalenyl]azo]-7-nitro-1-napthalene-sulfonic acid monosodium salt; diethylene triaminepentaacetic acid; 8-hydroxyquinoline; 8-hydroxyquinoline-5-sulfonic acid; maleic acid; citric acid; and N-[2-hydroxyethyl) imino-diacetic acid.

50. The bath of claim 49, wherein said chelating agent is ethylenediaminetetraacetic acid, disodium salt dihydrate having a concentration in solution of between about 0.5 and 1.25 Molar.

51. The bath of claim 46, further comprising means for detecting the de-activation of said bath.

52. The bath of claim 51, wherein said detecting means comprises color changing means for indicating an increase in pH of the bath.

53. A method for removing residual dental cement from a temporary dental prosthesis or appliance comprising:
preparing an aqueous bath containing a metal hydroxide with a concentration of between about 0.5 and 3.0 Molar and a chelating agent with a concentration of between about 0.25 and about 2.0 Molar; and
applying said aqueous bath to said temporary dental prosthesis or appliance to dissolve said residual dental cement.

54. The method of claim 53, wherein said preparing step comprises:
adding sodium hydroxide to said bath in a concentration of between about 1.0 and 2.0 Molar; and
adding ethylenediaminetetraacetic acid, disodium salt dihydrate to the bath in a concentration of between about 0.50 and 1.25 Molar.

55. For a dental cement composition containing a metal oxide, a metal hydroxide and an aqueous solution of a polycarboxylic acid, a method for dissolving said cement composition comprising applying to said cement composition an aqueous bath containing a metal hydroxide with a concentration of between about 0.5 and 3.0 Molar and a chelating agent with a concentration of between about 0.25 and 2.0 Molar.

56. A system for re-using a temporary dental prosthesis or appliance comprising:
a cement composition suitable for fixing said temporary dental prosthesis or appliance to dental tissue, said cement composition including a metal oxide in an amount between about 2 and 50 weight percent, a metal hydroxide in an amount between about 2 and 35 weight percent and an aqueous solution of a polycarboxylic acid in an amount between about 35 and 75 weight percent; and
a dissolving bath suitable for removing said cement composition from said temporary dental prosthesis or appliance, said bath comprising an aqueous solution containing a metal hydroxide having a concentration of between about 0.5 and 3.0 Molar and a chelating agent having a concentration of between about 0.25 and 2.0 Molar.

57. The system of claim 56, wherein said cement composition further includes:
a fatty acid in an amount between about 0.1 and 25 weight percent;
a polyvinylacetate emulsion in an amount between about 0.6 and 45 weight percent; and
a dimer fatty acid in an amount between about 0.2 and 25 weight percent.

58. The system of claim 56, wherein:
said metal oxide comprises zinc oxide in an amount between about 5 and 40 weight percent;
said cement composition metal hydroxide comprises calcium hydroxide in an amount between about 2 and 25 weight percent; and
said aqueous solution of a polycarboxylic acid comprises an aqueous solution of polyacrylic acid in an amount between about 35 and 60 weight percent.

59. The system of claim 58, wherein said cement composition further includes:
the fatty acid of lauric acid in an amount between about 0.3 and 10 weight percent;
polyvinylacetate copolymer with ethylene in an amount between about 2.0 and 25 weight percent; and
an unsaturated $C_{18}$ dimer fatty acid of oleic acid in an amount between about 0.5 and 15 weight percent.

60. The system of claim 56, wherein:
said bath metal hydroxide comprises sodium hydroxide having a concentration of between about 1 and 2 Molar; and
said chelating agent comprises ethylene diaminetetraacetic acid, disodium salt dihydrate having a concentration of between about 0.5 and 1.25 Molar.

61. A method for preparing a dental cement which is suitable as a fixing for a temporary dental prosthesis or appliance comprising:
combining a metal oxide in an amount between about 2 and 50 weight percent with a metal hydroxide in an amount between about 2 and 35 weight percent to form a paste component; and
adding a catalyst component comprising an aqueous solution of a polycarboxylic acid in an amount between about 35 and 75 weight percent to said paste component;
wherein said weight percents are based on the total weight of said dental cement.

62. The method of claim 61, wherein said combining step includes mixing a fatty acid in an amount between about 0.1 and 25 weight percent and a polyvinylacetate emulsion in an amount between about 0.3 and 15 weight percent with said metal oxide and said metal hydroxide in order to form said paste component.

63. The method of claim 62, wherein said combining step further includes mixing at least one plasticizer with said metal oxide, said metal hydroxide, said fatty acid and said polyvinylacetate compound in order to form said paste component.

64. The method of claim 51, further including the step of mixing a polyvinylacetate emulsion in an amount between about 0.3 and 30 weight percent and a dimer fatty acid in an amount between about 0.2 and 25 weight percent with said aqueous solution of a polycarboxylic acid prior to adding said catalyst component to said paste component.

65. A dental cement for providing a fixing for a temporary dental prosthesis or appliance comprising:
- a metal oxide in an amount between about 2 and 50 weight percent;
- a metal hydroxide in an amount between about 2 and 35 weight percent;
- an aqueous solution of a polycarboxylic acid in an amount between about 35 and 75 weight percent; and
- a $C_8$ to $C_{18}$ saturated fatty acid in an amount between about 0.1 and 25 weight percent.

66. The cement of claim 65, wherein the fatty acid is the fatty acid of lauric acid in an amount between about 0.3 and 10 weight percent.

67. A dental cement for providing a fixing for a temporary dental prosthesis or appliance comprising:
- a metal oxide in an amount between about 2 and 50 weight percent;
- a metal hydroxide in an amount between about 2 and 35 weight percent;
- an aqueous solution of a polycarboxylic acid in an amount between about 35 and 75 weight percent; and
- a polyvinylacetate emulsion in an amount between about 0.6 and 45 weight percent.

68. The cement of claim 67, wherein the polyvinylacetate emulsion is polyvinylacetate copolymer with ethylene in an amount between about 2 and 25 weight percent.

69. A dental cement for providing a fixing for a temporary dental prosthesis or appliance comprising:
- a metal oxide in an amount between about 2 and 50 weight percent;
- a metal hydroxide in an amount between about 2 and 35 weight percent; and
- an aqueous solution of a polyacrylic acid in an amount between about 35 and 60 weight percent.

70. The cement of claim 69, wherein said aqueous solution of polyacrylic acid includes polyacrylic acid having an average molecular weight of between about 40,000 and 80,000.

71. The cement of claim 69, wherein said aqueous solution of polyacrylic acid includes polyacrylic acid in an amount between about 35 and 60 weight percent as compared to the total weight of the aqueous solution.

72. The cement of claim 69, wherein:
- the metal oxide comprises zinc oxide in an amount between about 5 and 40 weight percent; and
- the metal hydroxide comprises calcium hydroxide in an amount between about 2 and 25 weight percent.

73. The cement of claim 72, further including:
- the fatty acid of lauric acid in an amount between about 0.3 and 10 weight percent;
- polyvinylacetate copolymer with ethylene in an amount between about 2.0 and 25 weight percent; and
- an unsaturated $C_{18}$ dimer fatty acid of oleic acid in an amount between about 0.5 and 15 weight percent.

74. A dental cement for providing a fixing for a temporary dental prosthesis or appliance comprising:
- a metal oxide in an amount between about 2 and 50 weight percent;
- a metal hydroxide in an amount between about 2 and 35 weight percent;
- an aqueous solution of a polycarboxylic acid in an amount between about 35 and 75 weight percent; and
- a dimer fatty acid in an amount between about 0.2 and 25 weight percent.

75. The cement of claim 74, wherein the dimer fatty acid is an unsaturated $C_{18}$ dimer fatty acid of oleic acid in an amount between about 0.5 and 15 weight percent.

* * * * *